United States Patent
Keating et al.

(10) Patent No.: US 11,896,506 B2
(45) Date of Patent: Feb. 13, 2024

(54) ADJUSTABLE MANDREL FOR FORMING STENT WITH ANTI-MIGRATION FEATURES

(71) Applicant: BOSTON SCIENTIFIC SCIMED, INC., Maple Grove, MN (US)

(72) Inventors: Thomas M. Keating, Galway (IE); Martyn G. Folan, Galway (IE); Thomas Holly, Galway (IE); Anthony Creane, Galway (IE); Paul E. Tierney, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1068 days.

(21) Appl. No.: 16/046,174

(22) Filed: Jul. 26, 2018

(65) Prior Publication Data

US 2019/0029850 A1 Jan. 31, 2019

Related U.S. Application Data

(60) Provisional application No. 62/537,761, filed on Jul. 27, 2017.

(51) Int. Cl.
*A61F 2/86* (2013.01)
*A61F 2/848* (2013.01)
(Continued)

(52) U.S. Cl.
CPC ............... *A61F 2/86* (2013.01); *A61F 2/848* (2013.01); *A61F 2/90* (2013.01); *B21D 37/00* (2013.01);
(Continued)

(58) Field of Classification Search
CPC ......... B31C 1/083; B31C 1/086; B31D 37/00; B21F 45/008; B21F 1/00; B21F 1/002;
(Continued)

(56) References Cited

U.S. PATENT DOCUMENTS 1,945,195 A * 1/1934 Kellems ................. H02G 1/081
140/92.1
5,238,004 A 8/1993 Sahatjian et al.
(Continued)

FOREIGN PATENT DOCUMENTS

CN 102362023 A 2/2012
DE 102013221450 A1 7/2014
(Continued)

OTHER PUBLICATIONS

International Search Report and Written Opinion dated Oct. 9, 2018 for International Application No. PCT/US2018/043863.

*Primary Examiner* — Debra M Sullivan
*Assistant Examiner* — Matthew Stephens
(74) *Attorney, Agent, or Firm* — Seager, Tufte & Wickhem, LLP

(57) ABSTRACT

A mandrel for forming a stent with a tapered profile and one or more anti-migration features includes a first stent shaping segment having a first diameter, a second stent shaping segment having a second diameter less than the first diameter and a tapered segment disposed therebetween. A third stent shaping segment is releasably securable to the second stent shaping segment and has a third diameter greater than the second diameter. One or more movable pins are outwardly extendable from corresponding apertures formed within the tapered segment. An actuation element is engagable with the first stent shaping segment and includes a tapered surface configured to engage the one or more movable pins and support the one or more movable pins extended from the corresponding apertures.

19 Claims, 17 Drawing Sheets

(51) Int. Cl.
*A61F 2/90* (2013.01)
*B21F 45/00* (2006.01)
*B31C 1/08* (2006.01)
*B21D 37/00* (2006.01)

(52) U.S. Cl.
CPC ............ *B21F 45/008* (2013.01); *B31C 1/083* (2013.01); *A61F 2240/001* (2013.01); *A61F 2240/005* (2013.01); *A61F 2250/0004* (2013.01); *A61F 2250/0039* (2013.01)

(58) Field of Classification Search
CPC .... B21D 41/026; B21D 41/028; B21D 39/20; B65H 75/246
USPC ....................... 140/123, 92.1; 87/34; 242/529
See application file for complete search history.

(56) References Cited

U.S. PATENT DOCUMENTS

| | | | |
|---|---|---|---|
| 5,662,713 | A | 9/1997 | Andersen et al. |
| 6,508,803 | B1 | 1/2003 | Horikawa et al. |
| 8,151,682 | B2 | 4/2012 | Lilburn et al. |
| 9,498,319 | B2 | 11/2016 | Walak |
| 2004/0098099 | A1* | 5/2004 | McCullagh .............. D04C 1/06 623/1.15 |
| 2004/0193141 | A1 | 9/2004 | Leopold et al. |
| 2005/0283962 | A1* | 12/2005 | Boudjemline ........... D04C 1/06 29/433 |
| 2009/0043373 | A1* | 2/2009 | Arnault De La Menardiere ........ A61F 2/848 623/1.15 |
| 2009/0151416 | A1* | 6/2009 | Obradovic ................ A61F 2/95 72/264 |
| 2009/0285925 | A1* | 11/2009 | Myers ..................... B29C 57/04 425/393 |
| 2010/0191319 | A1* | 7/2010 | Lilburn .................... D04C 1/06 623/1.15 |
| 2011/0082483 | A1* | 4/2011 | Diamant ........ A61B 17/320725 606/159 |
| 2011/0307070 | A1 | 12/2011 | Clerc et al. |
| 2016/0058585 | A1 | 3/2016 | Seddon et al. |
| 2016/0100930 | A1 | 4/2016 | Walsh et al. |
| 2016/0213498 | A1* | 7/2016 | Wang ...................... D04C 1/06 623/1.15 |
| 2020/0121444 | A1* | 4/2020 | White ...................... A61F 2/07 425/393 |

FOREIGN PATENT DOCUMENTS

| | | | | |
|---|---|---|---|---|
| GB | 2339837 | A | * 3/2004 | ............ B21D 39/04 |
| GB | 2512176 | A | 9/2014 | |
| KR | 20110119743 | A | 11/2011 | |
| KR | 20140094144 | A | 7/2014 | |
| WO | 2010085794 | A2 | 7/2010 | |

* cited by examiner

ADJUSTABLE MANDREL FOR FORMING STENT WITH ANTI-MIGRATION FEATURES

CROSS-REFERENCE TO RELATED APPLICATIONS

This application claims priority to U.S. Provisional Application Ser. No. 62/537,761, filed Jul. 27, 2017, the entirety of which is incorporated herein by reference.

TECHNICAL FIELD

The disclosure is directed to a mandrel for forming a stent having anti-migration features. More particularly, the disclosure is directed to an adjustable mandrel for forming a stent having anti-migration features.

BACKGROUND

A stent may be configured to be positioned in a body lumen for a variety of medical applications. For example, a stent may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some cases, a stent may include anti-migration features in order to help anchor the stent in place in whichever body lumen the stent is placed. In some instances, forming these anti-migration features may be difficult to do accurately and repeatedly.

BRIEF SUMMARY

The disclosure is directed to several alternative designs, materials and methods of manufacturing medical device structures and assemblies, and uses thereof. An example device for manufacturing a medical device structure is a mandrel to form an anti-migratory stent. The mandrel includes a mandrel body having a bore extending within the mandrel body as well as one or more apertures that are radially disposed about the mandrel body. One or more movable pins are outwardly extendable from the one or more apertures. The mandrel also includes an actuation element engagable with the bore extending within the mandrel body and including a tapered surface configured to engage the one or more movable pins, the actuation element being actuatable relative to the mandrel body such that the tapered surface supports the one or more movable pins extended from the one or more apertures.

Alternatively or additionally to any embodiment above, the mandrel body may include a first stent shaping segment having a first diameter, a second stent shaping segment having a second diameter less than the first diameter, and a tapered segment disposed between the first stent shaping segment and the second stent shaping segment.

Alternatively or additionally to any embodiment above, the mandrel may further include a third stent shaping segment releasably securable to the second stent shaping segment, the third stent shaping segment having a third diameter greater than the second diameter.

Alternatively or additionally to any embodiment above, the one or more movable pins may include a plurality of pins, and the one or more apertures may include a plurality of apertures such that there is a pin disposable within each of the plurality of apertures.

Alternatively or additionally to any embodiment above, at least some of the plurality of pins have equal lengths.

Alternatively or additionally to any embodiment above, the plurality of apertures are equally spaced circumferentially about the tapered segment.

Alternatively or additionally to any embodiment above, the corresponding apertures extend through the tapered segment and are configured to enable the pins to extend orthogonally to a tapered surface of the tapered segment.

Alternatively or additionally to any embodiment above, the corresponding apertures extend through the tapered segment and are configured to enable the pins to extend at varying angles relative to a tapered surface of the tapered segment.

Alternatively or additionally to any embodiment above, an end of each of the one or more movable pins includes a recessed slot configured to accommodate a wire of a stent being shaped on the mandrel.

Another example device is a mandrel for forming a stent with a tapered outer profile and anti-migration features, the mandrel including a mandrel body having a first stent shaping segment having a first diameter and a first threaded aperture extending within the first stent shaping segment, a second stent shaping segment having a second diameter less than the first diameter and a second threaded aperture extending within the second stent shaping segment and a tapered segment disposed between the first stent shaping segment and the second stent shaping segment, the tapered segment including a tapered surface. A plurality of apertures extend through the tapered surface. The mandrel includes a plurality of movable pins, each of the plurality of movable pins outwardly extendable from one of the plurality of apertures, the plurality of movable pins being configured to form the anti-migration features in the stent. The mandrel includes a mandrel cap that is releasably securable to the second stent shaping segment and that includes a third stent shaping segment having a third diameter greater than the second diameter. An actuation element includes a tapered end that is configured to engage the plurality of movable pins and a threaded body that is configured to threadedly engage the first threaded aperture. Rotating the actuation element causes the actuation element to advance into the first stent shaping segment such that the tapered end drives the plurality of movable pins in an outward direction.

Alternatively or additionally to any embodiment above, the third diameter is equal to the first diameter.

Alternatively or additionally to any embodiment above, at least some of the plurality of pins have equal lengths.

Alternatively or additionally to any embodiment above, at least some of the plurality of pins have differing lengths.

Alternatively or additionally to any embodiment above, an end of each of the plurality of movable pins includes a recessed slot configured to accommodate a wire of a stent being shaped on the mandrel.

Alternatively or additionally to any embodiment above, the plurality of apertures extend through the tapered segment and are configured to enable the pins to extend orthogonally to a tapered surface of the tapered segment.

Alternatively or additionally to any embodiment above, the plurality of apertures extend through the tapered segment and are configured to enable the pins to extend at varying angles relative to a tapered surface of the tapered segment.

An example method may be found in a method of manufacturing a stent having anti-migration features. A knitted stent blank may be disposed in position over a mandrel that includes a tapered outer surface and one or more anti-migration feature forming elements. A wire of the knitted stent blank may be engaged with the one or more anti-migration feature forming elements, and the woven stent blank may be annealed while disposed on the mandrel to form a shaped stent with the anti-migration feature. The one or more anti-migration feature forming elements may be disengaged in order to remove the shaped stent from the mandrel.

Alternatively or additionally to any embodiment above, the one or more anti-migration feature forming elements include pins that are configured to be driven in a radially outward direction relative to a central longitudinal axis of the mandrel, and engaging the wire with the one or more anti-migration feature forming elements includes driving the pins in the radially outward direction relative to the central longitudinal axis of the mandrel.

Alternatively or additionally to any embodiment above, disengaging the one or more anti-migration feature forming elements includes permitting the pins to move in a radially inward direction relative to the central longitudinal axis of the mandrel.

Alternatively or additionally to any embodiment above, disposing the knitted stent blank in position over the mandrel includes stretching the knitted stent blank over the mandrel and allowing the knitted stent blank to conform to the tapered outer surface of the mandrel.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
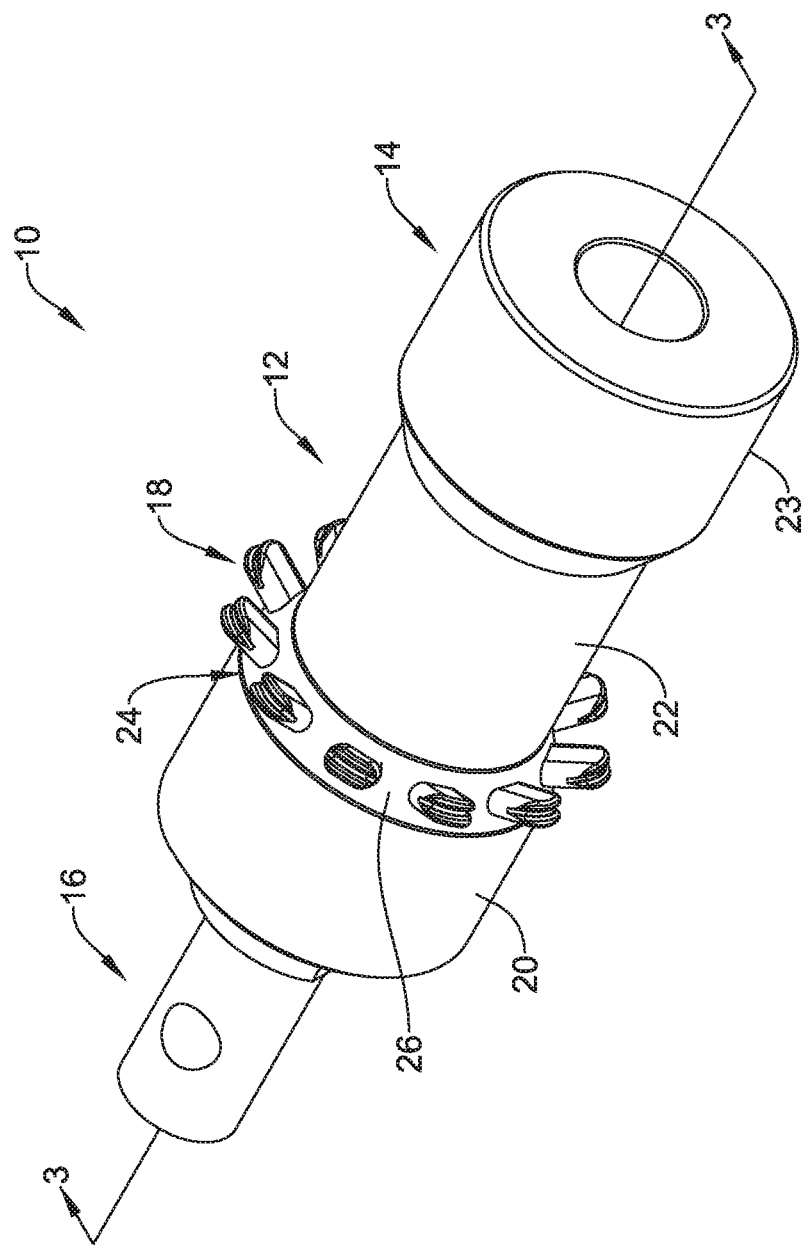
FIG. 1 is a perspective view of an adjustable mandrel in accordance with an embodiment of the disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a perspective view of a mandrel 10 for forming a stent having anti-migration features. In some instances, the stent may additionally include a tapered outer profile region with one or more flared end regions as well as anti-migration features. In some cases, the stent may be considered as having an hourglass profile, for example. However, in other instances, the stent may have a generally constant outer diameter with one or more anti-migration features extending radially outward therefrom.

Figure 2:
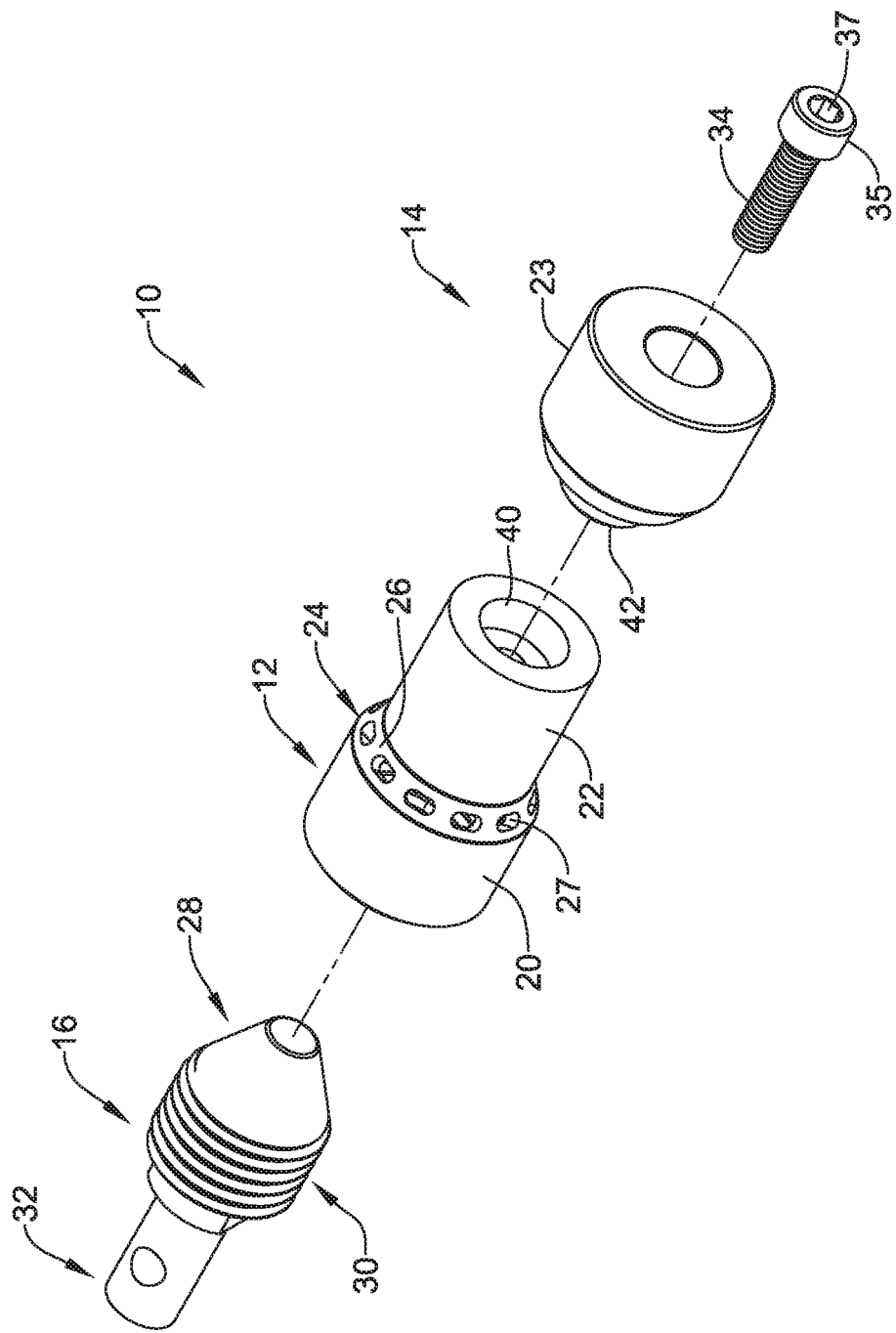
FIG. 2 is an exploded perspective view of the adjustable mandrel of FIG. 1.

As can be seen, the mandrel 10 includes a mandrel body 12, a mandrel cap 14, an actuation element 16 and a plurality of anti-migration feature forming pins 18. FIG. 2 is an exploded perspective view of the mandrel 10, with the anti-migration feature forming pins excluded for clarity. In some cases, the mandrel cap 14 may be releasably secured to the mandrel body 12 via a bolt 34, bayonet coupling, or other securement mechanism. In some instances, the mandrel cap 14 may be removable from the mandrel body 12 in order to facilitate removal of a stent from the mandrel 10. In other embodiments, the mandrel body 12 and the mandrel cap 14 may be formed as a unitary or monolithic structure, particularly if the mandrel cap 14 has an outer diameter roughly the same as an outer diameter of the mandrel body 12. In some instances, the mandrel body 12 may include a cylindrical portion having an outer diameter, whereas the mandrel cap 14 may have an outer diameter greater than the cylindrical portion of the mandrel body 12.

The mandrel body 12, shown in FIGS. 1 and 2, includes a first stent shaping segment 20 and a second stent shaping segment 22. The first stent shaping segment 20 may be a cylindrical portion of the mandrel body 12 having a first diameter, and the second stent shaping segment 22 may be a cylindrical portion of the mandrel body having a second diameter. In some cases, the first stent shaping segment 20 and/or the second stent shaping segment 22 may have a non-cylindrical profile. For example, the first stent shaping segment 20 and/or the second stent shaping segment 22 may instead have a polygonal cross-sectional profile such as an octagonal cross-sectional profile. This is just an example. The first diameter may be different than the second diameter. For example, the first diameter may be greater than the second diameter. A tapered segment 24 extends between the first stent shaping segment 20 and the second stent shaping segment 22 and defines a tapered surface 26 extending from a cylindrical outer surface of the first stent shaping segment 20 to a cylindrical outer surface of the second stent shaping segment 22. The tapered segment 24 includes a plurality of apertures 27 that extend through the circumferential wall of the tapered segment from the tapered surface 26 to an internal bore extending axially within the mandrel body 12 in order to accommodate the anti-migration feature forming pins 18. It will be appreciated that an angle of the tapered surface 26, relative to the first stent shaping segment 20 and/or the second stent shaping segment 22, may influence the relative angle at which the anti-migration feature forming pins 18 extend outwardly from the tapered surface 26.

In some cases, particularly if the first stent shaping segment 20 and the second stent shaping segment 22 have a similar or identical outer diameter, the tapered surface 26 may itself not be tapered, but may instead have a constant outer diameter. In some instances, at least some of the plurality of apertures 27 may have a major dimension that is orthogonal to the tapered surface 26. In some cases, at least some of the plurality of apertures 27 may have a major dimension that extends at an acute angle relative to the tapered surface 26. It will be appreciated that in some cases, some of the plurality of apertures 27 may extend at different angles relative to the tapered surface 26. As shown, the plurality of apertures 27 may be considered as being radially aligned in a ring that extends around the tapered segment 24. In some cases, it will be appreciated that some of the plurality of apertures 27 may be axially displaced relative to others of the plurality of apertures 27. In other words, some of the plurality of apertures 27 may form a first ring around the tapered segment 24 while others of the plurality of apertures 27 may form a second ring around that tapered segment 24 that is axially displaced from the first ring around the tapered segment 24.

In some cases, at least some of the plurality of apertures 27 may extend linearly through the tapered segment 24 such that each corresponding pin 18 extends through the aperture 27 orthogonally to the tapered surface 26. In some cases, at least some of the apertures 27 may have a curved or helical shape, such that as the corresponding pin 18, which may have a complementary curved or helical shape, is extended out of the aperture 27, the pin 18 may rotate, and thus a distal end of the pin 18 (such as the pin end 62) may move radially as well as axially.

The actuation element 16 may be configured to extend into the bore of the mandrel body 12 from one end of the mandrel body 12 (e.g., the end of the mandrel body opposite to the mandrel cap 14) to selectively engage and actuate the pins 18 within the apertures 27. For example, the actuation element 16, shown in FIG. 2, includes a tapered end 28 that, as will be illustrated in subsequent Figures, may be configured to engage the anti-migration feature forming pins 18, as well as a threaded body 30 that is configured to threadably engage a threaded aperture extending within the first stent shaping segment 20 of the mandrel body 12. In some instances, the tapered end 28 may be conically, frustoconically, convexly, or concavely tapered. The actuation element 16 may be considered as including a handle 32 that may be used by an individual or a machine to rotate the actuation element 16 and thus advance the actuation element 16 into the bore of the mandrel body 12 by rotating in a first direction or withdraw the actuation element 16 from the bore of the mandrel body 12 by rotating in a second, opposite direction. Thus, the threaded body 30 may threadably engage a threaded region of the bore of the mandrel body 12 to threadably advance the actuation element 16 into the bore (e.g., toward the mandrel cap 14) by rotating the actuation element 16 in a first rotational direction and withdraw the actuation element 16 from the bore (e.g., away from the mandrel cap 14) by rotating the actuation element 16 in a second, opposite rotational direction. This may be demonstrated, for example, with respect to FIGS. 3 and 4, which are cross-sectional views showing the actuation element 16 fully extended into the bore of the mandrel body 12 (FIG. 3) or partially extended (FIG. 4) taken along line 3-3 of FIG. 1. In other cases, it is contemplated that rather than the actuation element 16 itself including a threaded region, a threaded fastener may be configured to engage a threaded bore of the mandrel body 12 to actuate the actuation element 16 relative to the mandrel body 12.

Figure 3:
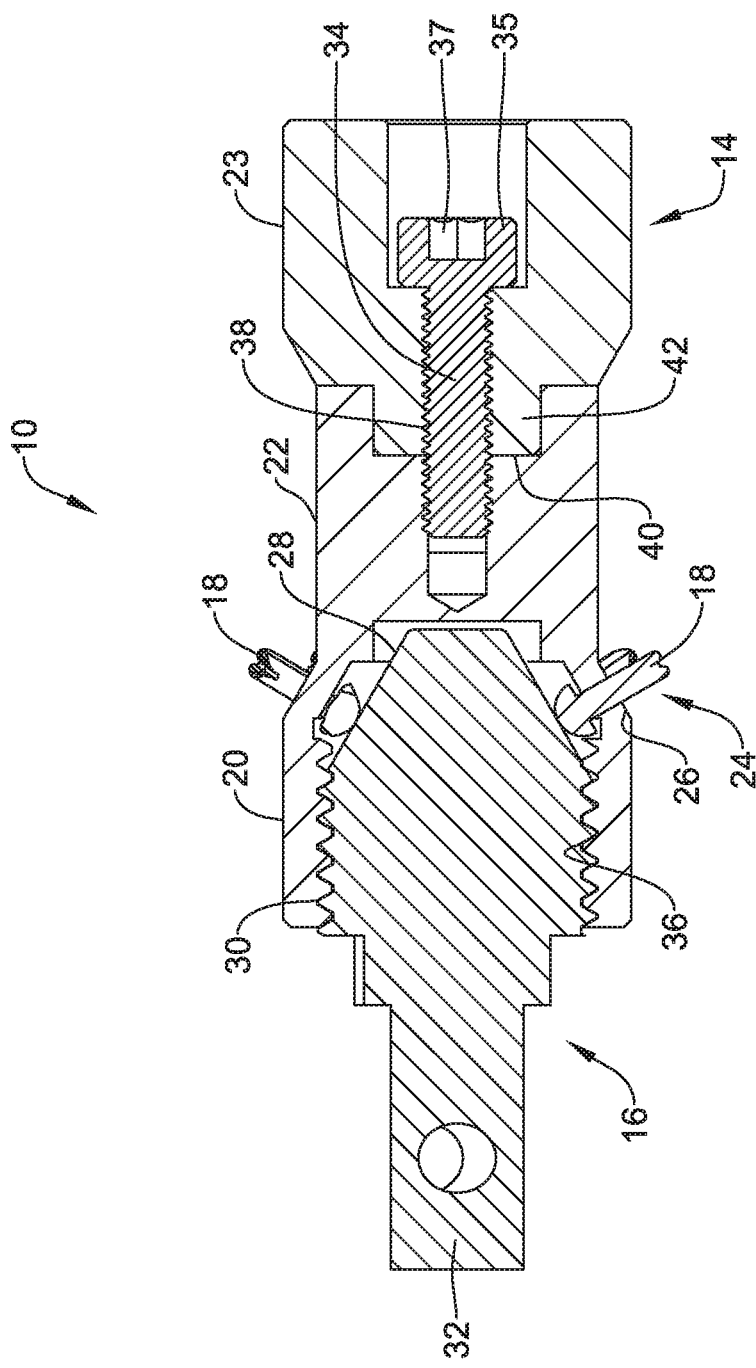
FIG. 3 is a cross-sectional view of the adjustable mandrel of FIG. 1, with the anti-migration feature forming pins shown in a fully extended position in accordance with an embodiment of the disclosure.

FIG. 3 shows the actuation element 16 fully extended into the bore of the mandrel body 12 with the threaded body 30 threadably engaged with the threaded region of the bore of the mandrel body 12. In particular, the bore of the mandrel body 12 includes a first threaded region 36 extending into the first stent shaping segment 20 of the mandrel body 12 from a first end of the mandrel body 12 that is configured, in diameter, depth and thread pitch, to threadedly engage the threaded body 30 of the actuation element 16. In some instances, as illustrated, the mandrel body 12 also includes a second threaded bore or region 38 extending into the second stent shaping segment 22 of the mandrel body 12 from the second, opposite end of the mandrel body that is configured, in diameter depth and thread pitch, to threadedly engage threads on the threaded fastener (e.g., bolt or screw)

34 in order to releasably secure the mandrel cap 14 in position relative to the mandrel body 12 at the second end of the mandrel body 12. In some cases, it is contemplated that rather than utilizing a separate threaded fastener 34, that the mandrel cap 14 itself may include a threaded protuberance that is configured to engage the second threaded bore 38. Alternatively, it is also contemplated that the second end of the mandrel body 12 may include a threaded protuberance, and the mandrel cap 14 may include a threaded bore or aperture to engage the threaded protuberance of the mandrel body 12, or a through hole for passing the threaded protuberance through to be threadedly engaged with a mating threaded fastener (e.g., nut) on an opposite side of the mandrel cap 14. In either event, the mandrel cap 14 may be secured to or removed from the mandrel body 12, particularly for aid in removing a formed stent from the mandrel 10. In some cases, the mandrel cap 14 may be permanently secured to the mandrel body 12, particularly in cases where the mandrel 10 has a profile in which an outer diameter of each successive stent shaping segment is equal to or less than an outer diameter of a preceding stent shaping segment and a formed stent may simply be slid off the mandrel 10 without removing the mandrel cap 14. In some cases, the mandrel body 12 may include a locating or centering aperture 40 that is configured to accommodate a locating or centering feature 42 extending from the mandrel cap 14, but this is not required in all cases. In some cases, rather than using the fastener 34 to secure the mandrel cap 14 to the mandrel body 12, the locating or centering feature 42 may itself threadedly engage the locating or centering aperture 40.

Figure 4:
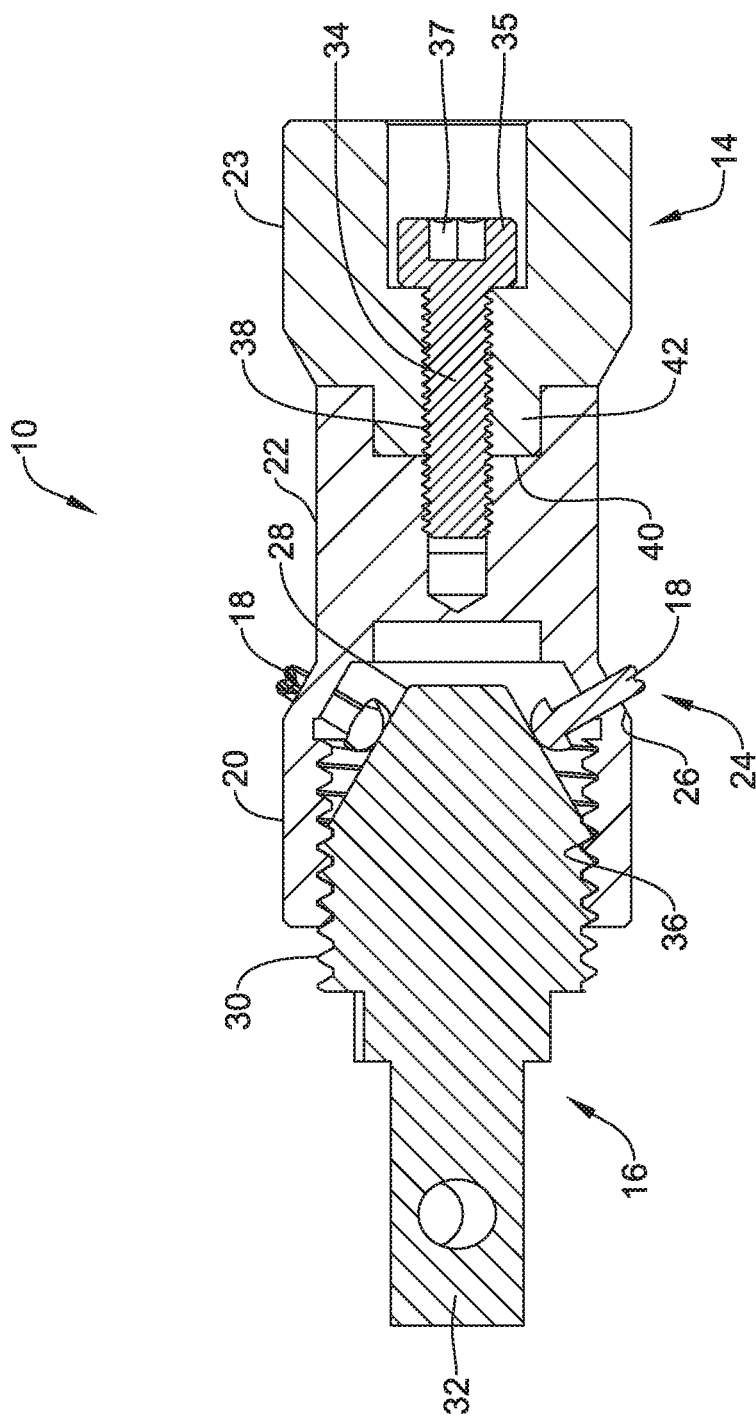
FIG. 4 is a cross-sectional view of the adjustable mandrel of FIG. 1, with the anti-migration feature forming pins shown in a partially extended position in accordance with an embodiment of the disclosure.

As seen in FIG. 3, the actuation element 16 is fully extended into the first threaded region 36 of the bore of the mandrel body 12. As a result, the anti-migration feature forming pins 18 can be seen as being extended radially outwardly through the corresponding apertures 27. In some cases, depending on the particular dimensions of the various components forming the mandrel 10, the anti-migration feature forming pins 18 may be considered as being extended radially outwardly as far as they can go before the actuation element 16 is fully extended into the first threaded region 36 of the bore of the mandrel body 12. A base 44 of each pin 18 may be seen as engaging the tapered end 28 of the actuation element 16. This can be contrasted with FIG. 4, in which the actuation element 16 is only partially extended into the first threaded region 36 of the bore of the mandrel body 12. Accordingly, while the base 44 of each pin 18 (only 2 pins are shown for clarity) is still engaged with the tapered end 28 of the actuation element 16, it can be seen that the pins 18 do not extend radially outwardly through the corresponding apertures 27 as far as the pins 18 extend in FIG. 3. In some cases, as shown in FIGS. 3 and 4, the base 44 of each pin 18 may be larger in at least one dimension than a diameter of the corresponding aperture 27. Thus, the extent that the pins 18 can be extended radially outward through the apertures 27 may be limited when the base 44 of the pin 18 abuts a peripheral edge of the aperture 27. As a result, the pins 18 are retained within the apertures 27, and won't fall out. The pins 18 can, in some instances, be removed completely by withdrawing the actuation element 16 from the bore of the mandrel body 12, permitting the pins 18 to move radially inward of the apertures 27 and then fall into the bore of the mandrel body 12.

Figure 5:
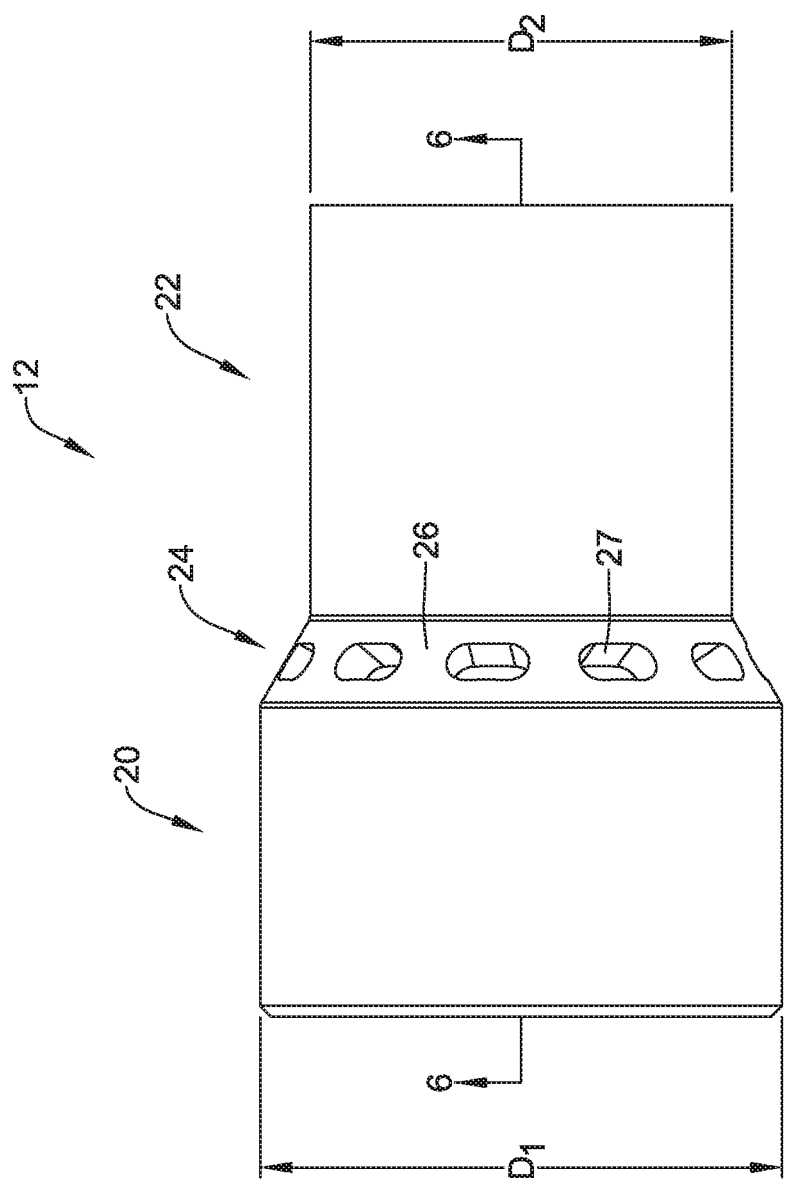
FIG. 5 is a side view of a mandrel body forming a portion of the adjustable mandrel of FIG. 1 in accordance with an embodiment of the disclosure.
Figure 6:
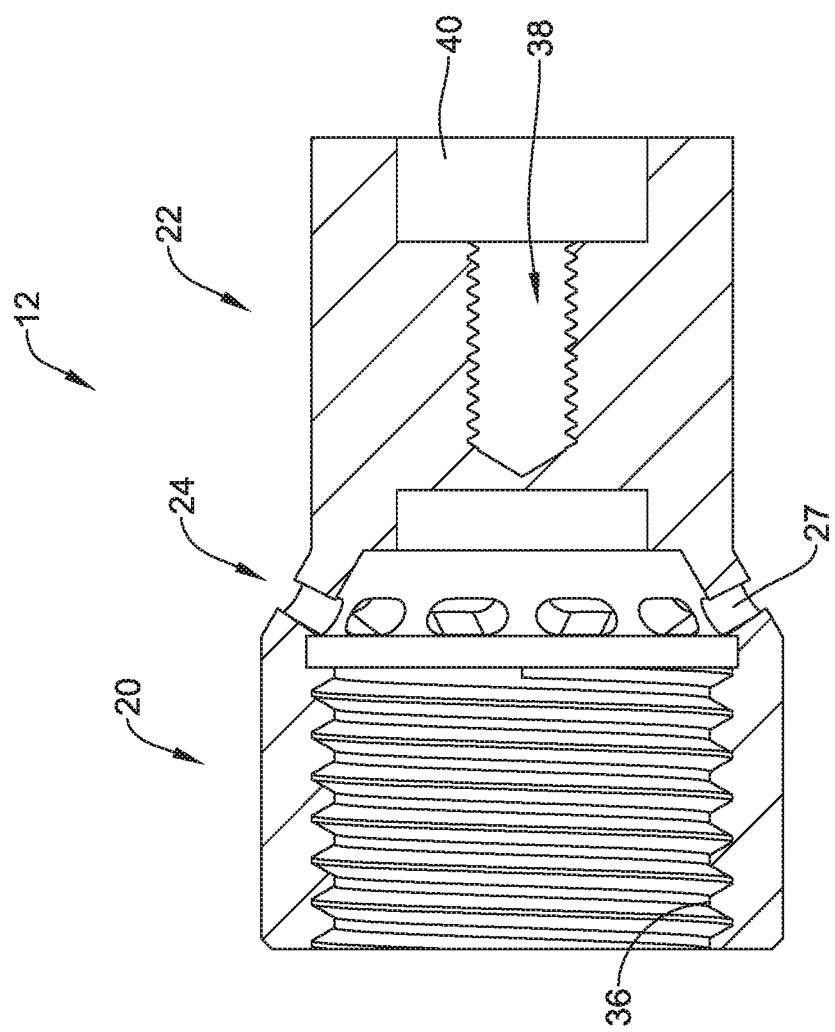
FIG. 6 is a cross-sectional view of the mandrel body of FIG. 5.

FIG. 5 is a side view of the mandrel body 12 and FIG. 6 is a cross-sectional view thereof, taken along the 6-6 line in FIG. 5. As can be seen, the first stent shaping segment 20 has a first diameter D1 and the second stent shaping segment 22 has a second diameter D2 that is less than the first diameter D1. In other cases, the second diameter D2 may be equal to the first diameter D1, or the second diameter D2 may be greater than the first diameter D1. In some cases, while a first stent shaping segment 20 and a second stent shaping segment 22 are shown, it will be appreciated that the mandrel body 12 may include a third stent shaping segment, a fourth stent shaping segment, and so on, depending on the desired profile of the final stent product. As will be appreciated, in the illustrated embodiment, the tapered segment 24 has a diameter (not labeled) that tapers smoothly from D1 to D2. In some cases, it is contemplated that the tapered segment 24 may instead have one or more step-wise changes in diameter. Furthermore, it can be seen that the plurality of apertures 27 may be uniformly spaced circumferentially around the perimeter (e.g., circumference) of the tapered segment 24. However, in other instances at least some of the plurality of apertures 27 may be non-uniformly spaced circumferentially around the perimeter (e.g., circumference) of the tapered segment 24. In some cases, at least some of the plurality of apertures 27 may be axially displaced relative to others of the plurality of apertures 27.

Figure 7:
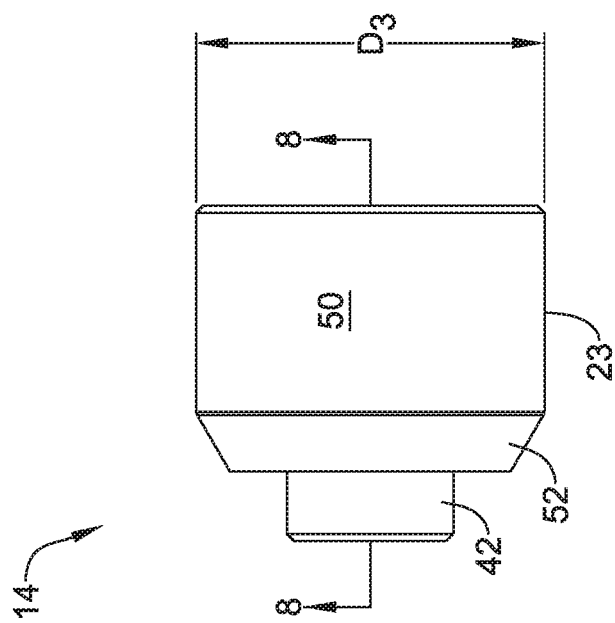
FIG. 7 is a side view of a mandrel cap forming a portion of the adjustable mandrel of FIG. 1 in accordance with an embodiment of the disclosure.
Figure 8:
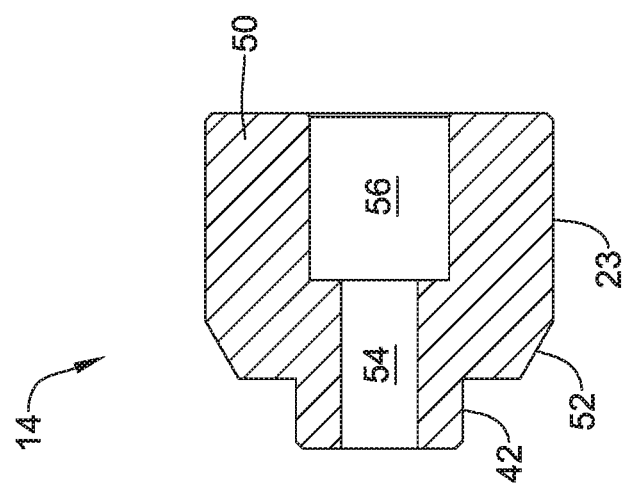
FIG. 8 is a cross-sectional view of the mandrel cap of FIG. 7.

FIG. 7 is a side view of the mandrel cap 14 and FIG. 8 is a cross-sectional view thereof, taken along the 8-8 line of FIG. 7. In some cases, the mandrel cap 14 includes a mandrel cap body 50 and a tapered section 52. The mandrel cap 14 may be considered as providing a third stent shaping segment 23 having a third diameter D3. In some cases, the diameter D3 may be the same as the diameter D1 (of the first stent shaping segment 20). In some instances, the diameter D3 may be either larger or smaller than the diameter D1, depending on the desired properties and dimensions of the stent to be produced using the mandrel 10. In some cases, the tapered section 52 varies smoothly in diameter between the diameter D3 and the diameter D2 (of the second stent shaping segment 22). In other cases, it is contemplated that the tapered section 52 may instead have one or more step-wise changes in diameter. In some instances, as shown for example in FIG. 8, the mandrel cap 14 may include an aperture 54 that is dimensioned to accommodate the fastener 34, as well as a larger aperture 56 that accommodates the fastener head 35 of the fastener 34. In some cases, the fastener head 35 of the fastener 34 may be configured to accommodate a tool such as but not limited to an Allen wrench, and thus may include a six or eight sided aperture 37.

Figure 9:
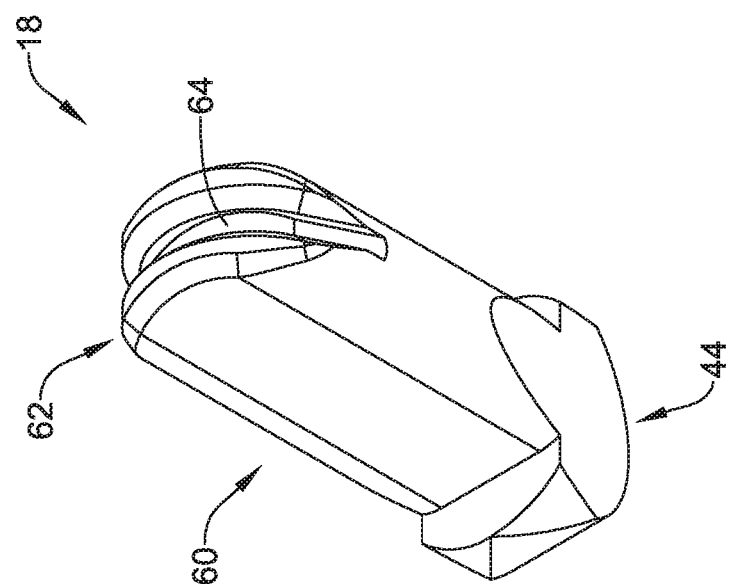
FIG. 9 is a perspective view of an anti-migration feature forming pin forming a portion of the adjustable mandrel of FIG. 1 in accordance with an embodiment of the disclosure.

FIG. 9 is a perspective view of one example of an anti-migration feature forming pin 18. In some cases, the pin 18 may include a pin body 60 extending between the base 44 (which may have an enlarged cross-section relative to the pin body 60) and a pin end 62 opposite the base 44. As noted, the base 44 may be larger in diameter than the pin body 60, but this is not required in all cases. In some cases, the pin end 62 may be curved to facilitate a portion of a wire of a stent to be formed in a curved shape. In some cases, the curved shape may be a simple curve. In some instances, the curved shape may be a compound curve, such as an undulating or wave-like shape. In some instances, the pin end 62 may include a recessed slot 64 that may be configured to accommodate a wire or wires of the stent being shaped on the mandrel 10. In some cases, the recessed slot 64 may itself have a simple or compound curve shape to instill a corresponding simple or compound curve shape to a stent wire extending through the recessed slot 64. For example, in some embodiments the recessed slot 64 may be a curved slot 64 providing a wire placed therein with a curved region. In some cases the recessed slot 64 may include two converging portions converging at a point at the pen end 62 to provide a wire with a sharp bend for an anti-migration feature. In some cases, the stent being formed is a knitted stent, and a constant diameter knitted stent blank may be stretched over the mandrel 10, with a particular wire of the knitted stent blank disposed within the recessed curved slot 64 in order to form an anti-migration feature extending radially outward from a knitted tubular wall of the stent. In some cases, the stent being formed is a braided stent, and may be braided in place on the mandrel 10, with a particular wire forming an anti-migration feature braided within the recessed curved slot 64 and extending radially outward from the braided tubular wall of the stent.

While the pin end 62 is illustrated as a curved profile and being no larger in dimension than the pin body 60, in some cases it is contemplated that the pin end 62 may extend laterally beyond the pin body 60 and form an arcuate surface. In some cases, for example, the arcuate surface of each of the pin ends 62 may align end to end, and essentially form a raised ring extending around the mandrel 10. The individual arcuate surfaces of each of the pin ends 62 maybe driven outward by extending the actuation element 16 into the mandrel body 12 by rotating the actuation element 16 in a first rotational direction in order to form a raised ring anti-migration feature in the stent. Rotating the actuation element 16 in a second, opposing rotational direction, allows the pins 18 to retract, and allow removal of the stent from the mandrel 10.

Figure 10:
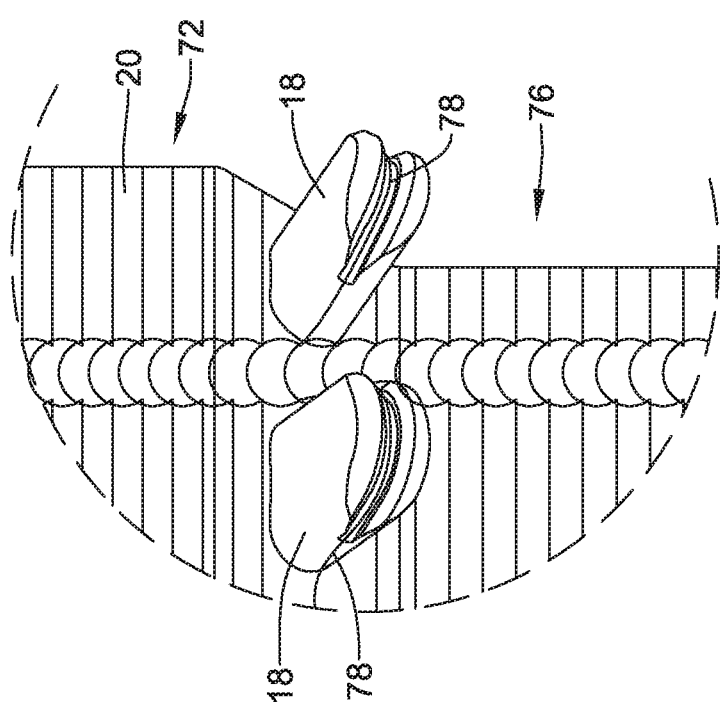
FIG. 10 is a side view of a portion of the adjustable mandrel of FIG. 1, showing a portion of a knitted stent disposed about the adjustable mandrel in accordance with an embodiment of the disclosure.
Figure 11:
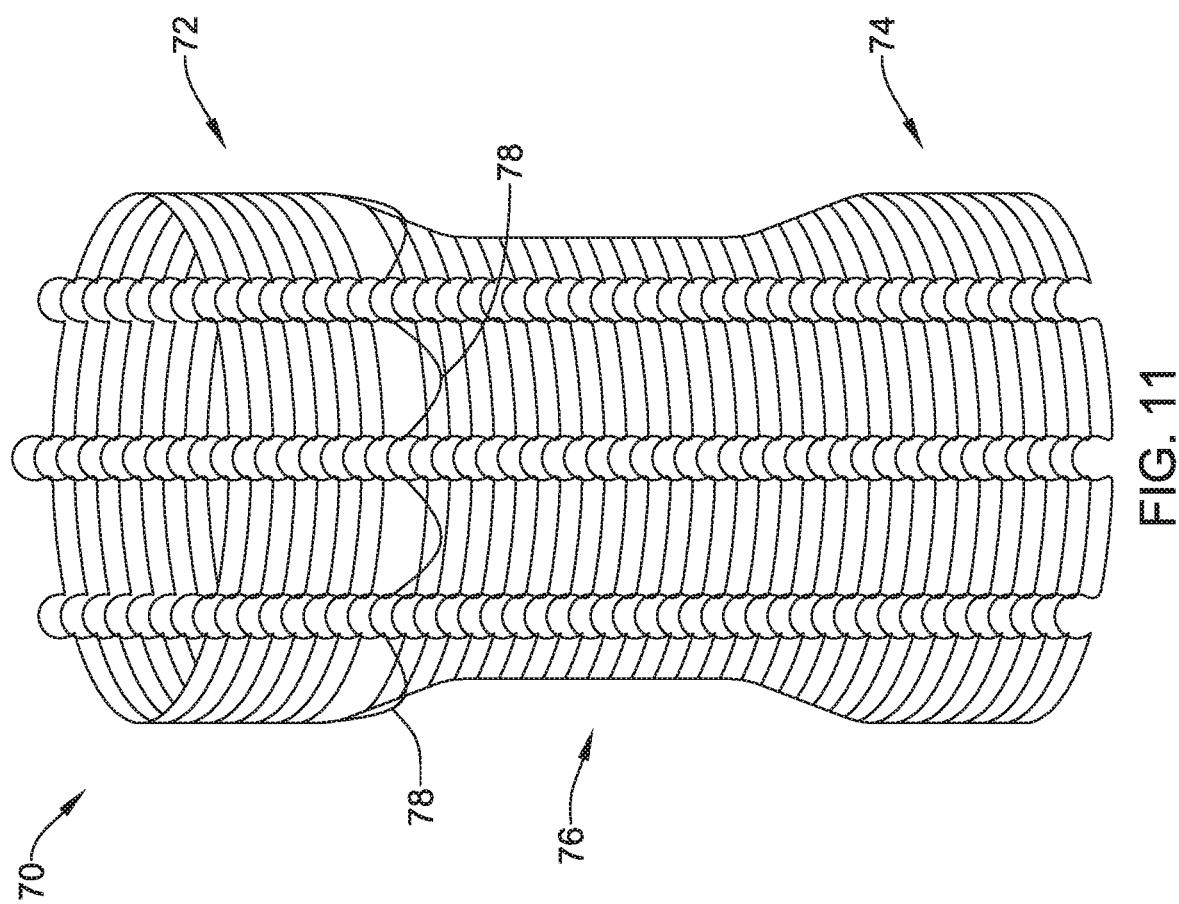
FIG. 11 is a side view of the knitted stent of FIG. 10, removed from the adjustable mandrel.

FIG. 10 shows a portion of a knitted stent 70 disposed on the mandrel 10, while FIG. 11 shows the knitted stent 70 removed from the mandrel 10. As shown in FIG. 10, one of the wires of the knitted stent may extend radially outward from the knitted tubular wall of the stent 70 and along the recessed slot 64 of the pin 18 to form one or more of the anti-migration features 78 of the stent 70. In some cases, a knitted stent such as the knitted stent 70 may be formed by first knitting a constant diameter stent blank (not illustrated), then stretching the constant diameter stent blank over the mandrel 10 prior to a shaping process and/or an annealing process. It can be seen that the knitted stent 70 has a first enlarged diameter portion 72 proximate a first end of the knitted stent 70 that corresponds to the first stent shaping segment 20, a second enlarged diameter portion 74 proximate a second end of the knitted stent 70 that corresponds to the third stent shaping segment 23, and a (relatively) reduced diameter portion 76 (e.g., a cylindrical body region intermediate the first and second enlarged diameter portions 72, 74) that corresponds to the second stent shaping segment 22. The knitted stent 70 includes anti-migration features 78 that correspond to the pins 18 which are arranged circumferentially around the knitted stent 70 at a transition region between the first enlarged dimeter portion 72 and the reduced diameter portion 76. However, it is contemplated that the anti-migration features 78 may be arranged at a different location along the length of the knitted stent 70, if desired. The pins 18 may be actuated radially outward with the wires disposed in the recessed slots 64 after the knitted stent black has been placed on the mandrel 10 to cause the portions of the wires engaged with the pins 18 to be urged radially outward from the knitted tubular wall of the stent to form the anti-migration features 78.

Figure 12A:
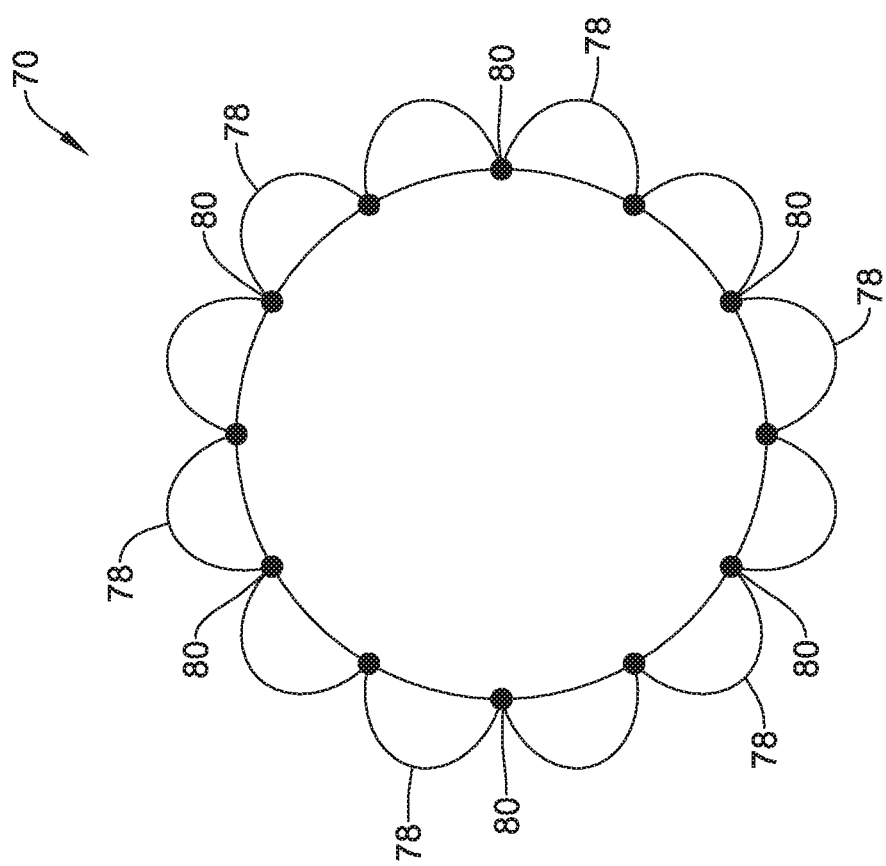
FIGS. 12A through 12D are schematic illustrations of anti-migration features that the knitted stent of FIG. 11 may include in accordance with embodiments of the disclosure.

FIG. 12A is an end view of the knitted stent 70, showing the anti-migration features 78 extending radially outward from the knitted tubular wall of the knitted stent 70. As illustrated, each of the anti-migration features 78 are loops of the filament(s) or wire(s) forming the knitted stent 70 extending between adjacent anchor points 80, each loop being roughly equal in shape and dimension. Anchor points 80 may be location in which portions of the filament(s) or wire(s) cross or loop around another portion of the filament (s) or wire(s). In other cases, some of the anti-migration features 78 may vary in shape and/or dimension, or may not be equally spaced, for example. While the anti-migration features 78 are shown as being curved, in some cases the anti-migration features 78 may be pointed, or include a flattened region, for example.

Figure 12B:
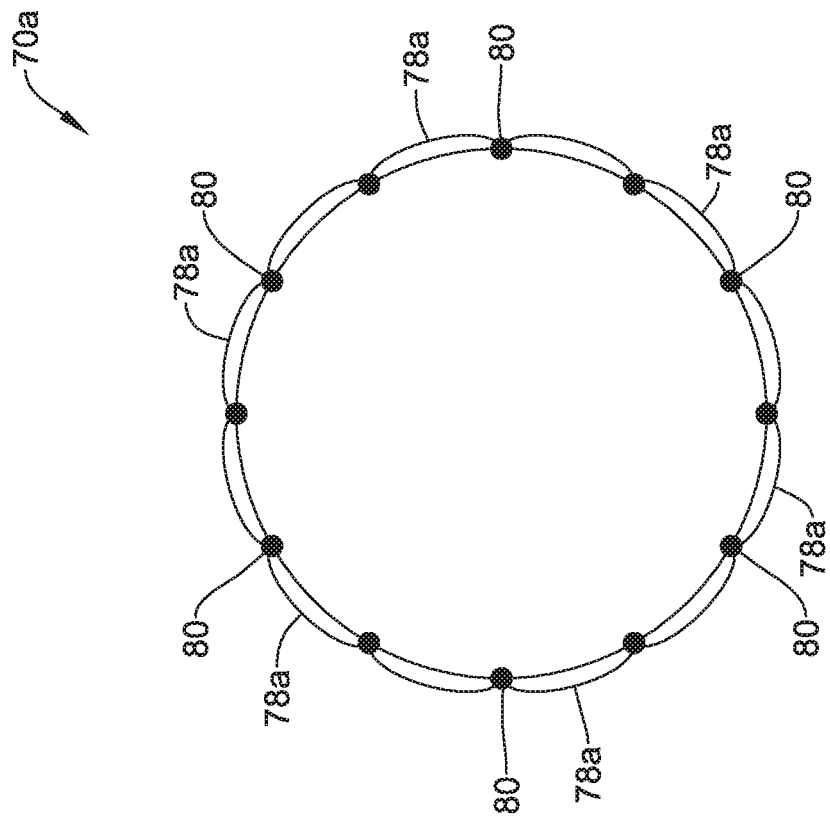

FIG. 12B, for example, shows a knitted stent 70a that includes a number of anti-migration features 78a. The anti-migration features 78a each extend between adjacent anchor points 78, and are each roughly equal in shape and dimension. However, by comparing FIG. 12B with FIG. 12A, it can be seen that the anti-migration features 78 shown in FIG. 12A extend radially outward further than the anti-migration features 78a shown in FIG. 12B. The anti-migration features 78a may be formed, for example, by using anti-migration feature forming pins 18 that are shorter in length, or by not advancing the actuation element 16 as far into the mandrel body 12, thus not advancing the pins 18 radially outward as far from the surface of the tapered segment 24 of the mandrel body 12. The anti-migration features 78a may be pointed, for example, or have other shapes as well.

It will be appreciated that the relative dimensions of the anti-migration features 78 and the anti-migration features 78a may be a function of the ultimate end-use of the knitted stent 70 (or 70a). Relatively larger anti-migration features 78, 78a may be useful in situations where the knitted stent 70 (or 70a) will be placed in anatomical locations where the knitted stent 70 (or 70a) may be subjected to relatively stronger migration forces and/or anatomical locations where the dimensions of the patient's anatomy are more variable. Relatively smaller anti-migration features 78, 78a may be useful in situations where the knitted stent 70 (or 70a) may be subjected to relatively weaker migration forces and/or anatomical locations where the dimensions of the patient's anatomy are less variable. In some cases, the overall dimensions of the knitted stent 70 (or 70a) may play a part as well. In some cases, for example, a larger diameter knitted stent 70 (or 70a) may have relatively larger anti-migration features 78, 78a while a smaller diameter knitted stent 70 (or 70a) may have relatively smaller anti-migration features 78, 78a.

Figure 12C:
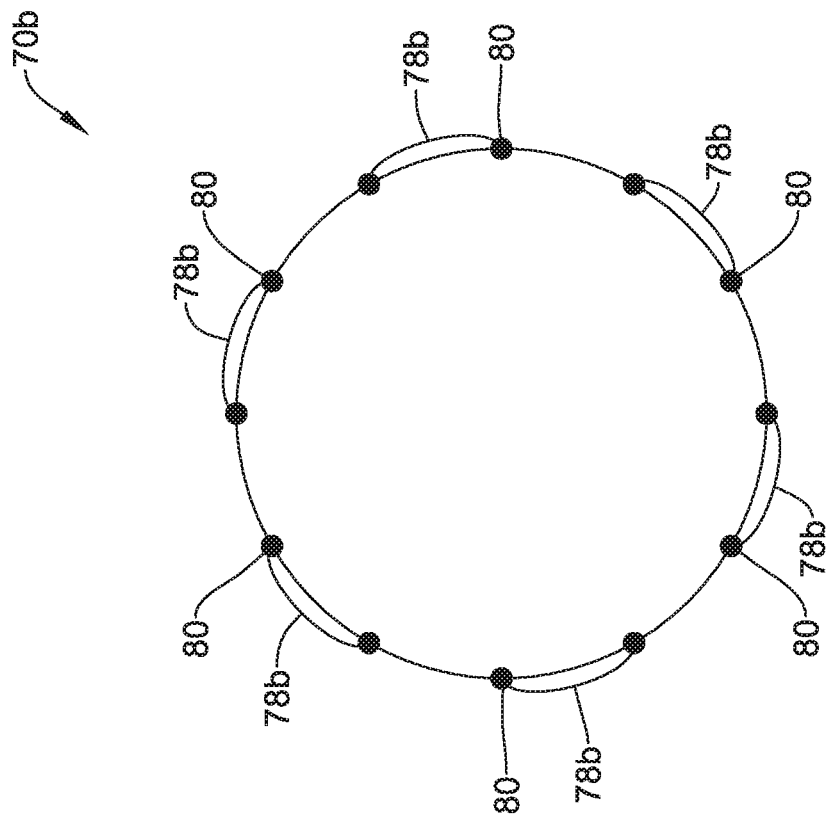

FIG. 12C shows a knitted stent 70b that includes a number of anti-migration features 78b. In contrast to the knitted stents 70 and 70a shown in FIGS. 12A and 12B, the anti-migration features 78b are unequally spaced about the periphery of the knitted stent 78b. Each of the anti-migration features 78b extend between adjacent anchor points 80, although some anchor points 80 are not attached to an anti-migration feature 78b. As illustrated, each of the anti-migration features 78b are roughly equal in shape and dimension. The anti-migration features 78b may be formed, for example, by only placing anti-migration feature forming pins 18 into some of the apertures 27. In some cases, it is contemplated that some of the anti-migration features 78b may be smaller or larger in dimension, and/or may vary in shape, relative to others of the anti-migration features 78b.

Figure 12D:
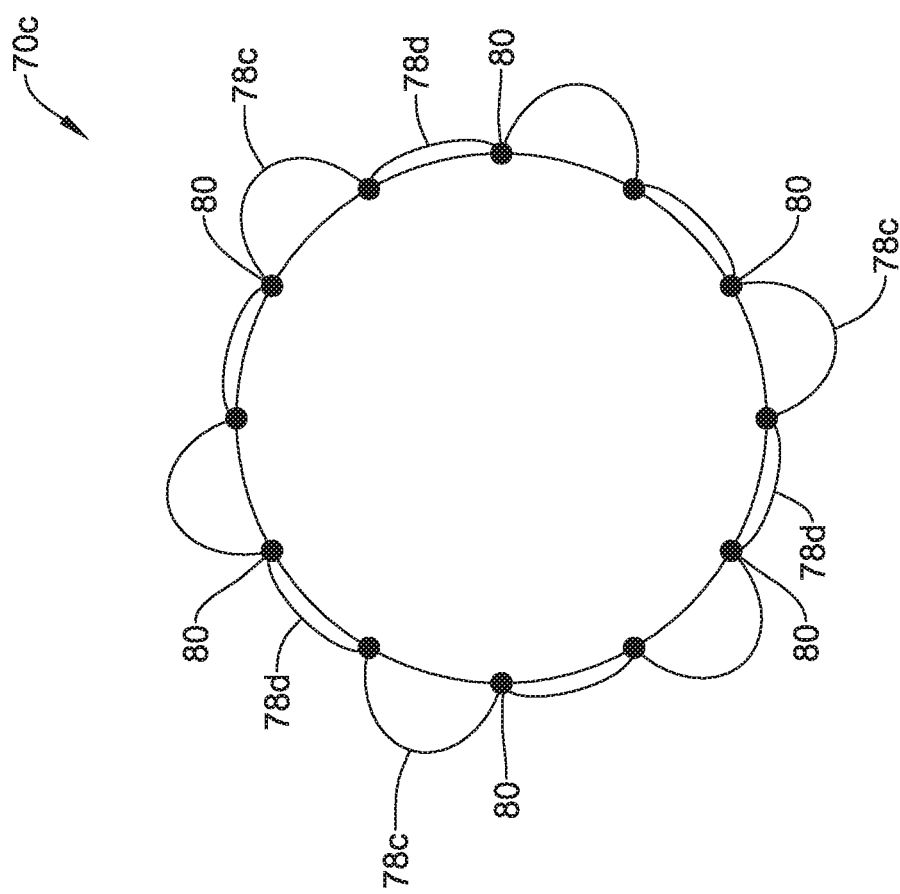

FIG. 12D shows a knitted stent 70c that includes a number of anti-migration features 78c and a number of anti-migration features 78d, each extending between adjacent anchor points 80. It will be appreciated that as illustrated, each of the anti-migration features 78c are roughly equal in shape and dimension, and each of the anti-migration features 78d are roughly equal in shape and dimension, albeit not extending radially outward as far as the anti-migration features 78c. The anti-migration features 78c and 78d may be formed, for example, by using a longer length pin 18 to form each of the anti-migration features 78c and a shorter length pin 18 to form each of the anti-migration features 78d. It will be appreciated that the particular anti-migration features 78, 78a, 78b, 78c and 78d are merely illustrative, and may be mixed or matched in any desired pattern.

Figure 13:
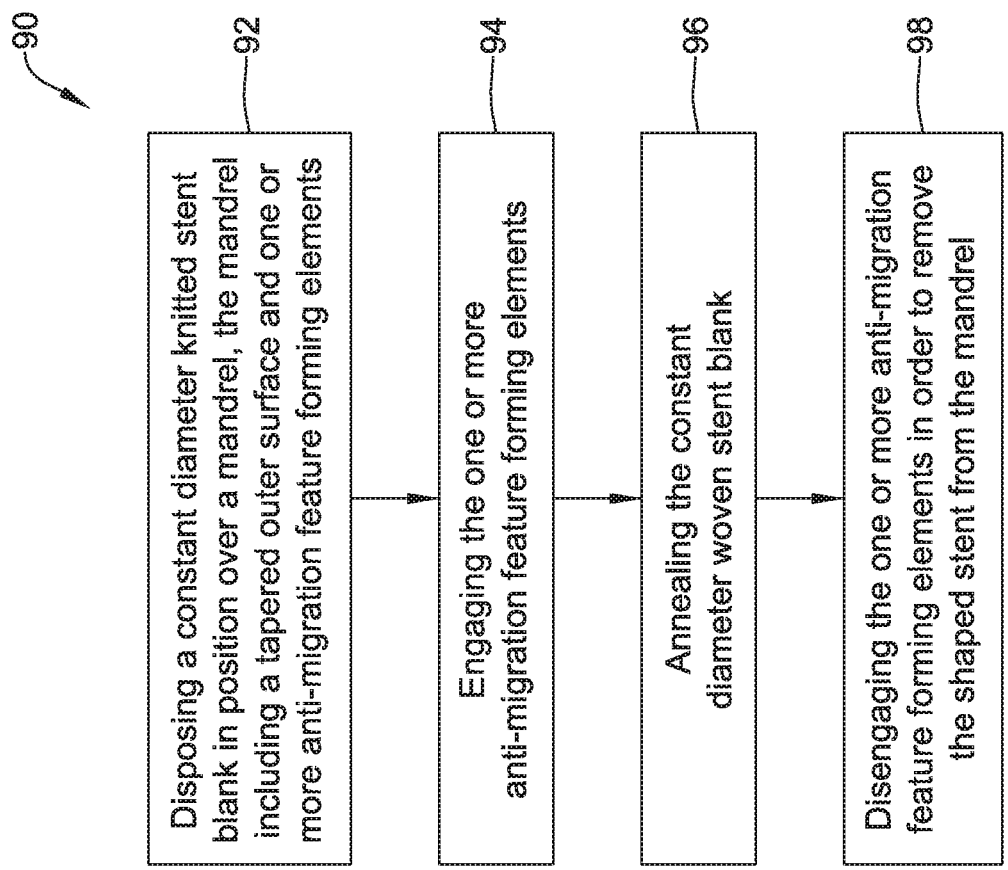
FIG. 13 is a flow diagram showing a method of forming the knitted stent of FIG. 11 in accordance with an embodiment of the disclosure.

FIG. 13 is a flow diagram showing a method 90 of forming a knitted stent having a non-uniform profile and one or more anti-migration features. In some cases, a constant diameter knitted stent blank may be positioned over a mandrel having a tapered outer surface and one or more anti-migration feature forming elements, as generally indicated at block 92. The mandrel may be the mandrel 10, for example. In some cases, disposing a constant diameter knitted stent blank in position over a mandrel includes stretching the constant diameter knitted stent blank over the mandrel and allowing the constant diameter knitted stent blank to conform to the varied diameter outer surface of the mandrel, such conforming to the various constant diameter regions and/or tapered diameter regions of the mandrel.

The one or more anti-migration feature forming elements (such as but not limited to the pins 18) may be engaged, as noted at block 94, in order to provide a desired shape prior to annealing, as indicated at block 96. In some cases, the one or more anti-migration feature forming elements are pins that are configured to be driven in a radially outward direction relative to the outer surface of the mandrel, and engaging the one or more anti-migration feature forming elements includes driving the pins in radially outward direction relative to the mandrel to urge the wire(s) or filament(s) engaged with the end of each of the pins in a radially outward direction relative to the knitted tubular structure of the stent. The mandrel and the stent thereon, with the anti-migration features formed, may then be subjected to an annealing or shape setting process. As seen at block 98, after the annealing or shape setting process, the one or more anti-migration feature forming elements may be disengaged in order to remove the shaped stent from the mandrel. In some cases, disengaging the one or more anti-migration feature forming elements comprises permitting the pins to move in an inward direction relative to the mandrel.

Figure 14:
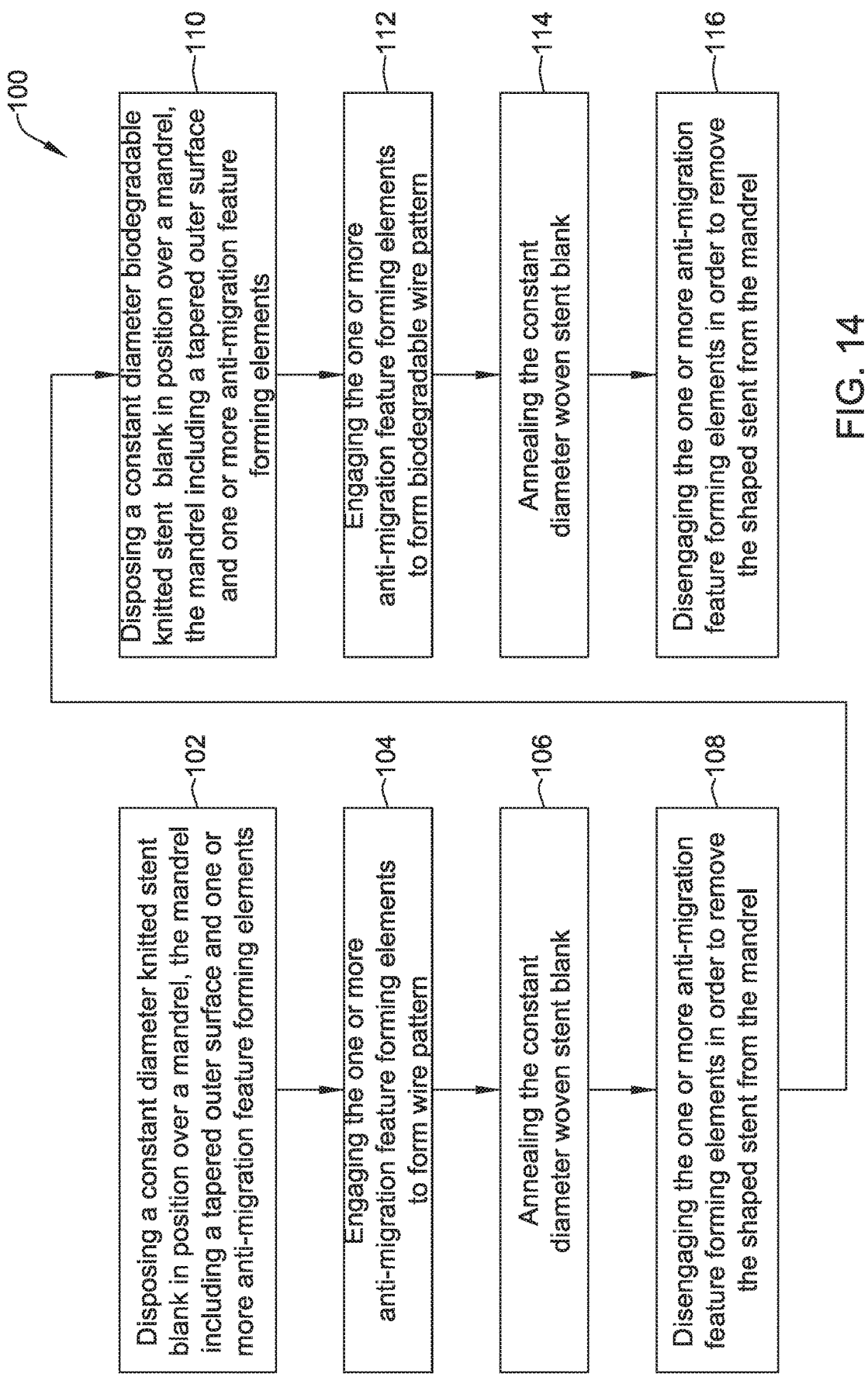
FIG. 14 is a flow diagram showing a method of forming a knitted stent having a non-uniform profile and one or more anti-migration features in accordance with an embodiment of the disclosure.

FIG. 14 is a flow diagram showing a method 100 of forming a knitted stent having a non-uniform profile and one or more anti-migration features. In some cases, the knitted stent may have a metallic component and a non-metallic or even biodegradable component. The metallic component and the non-metallic component may individually be shaped, and then combined to form a stent. In some cases, each of the metallic component and the non-metallic or even biodegradable component may each include anti-migration features, where the anti-migration features of the non-metallic or even biodegradable component complement the anti-migration features of the metallic component. In cases where the non-metallic component is biodegradable, the biodegradable anti-migration features may provide additional resistance to migration upon initial implantation of the stent, but dissolve away over time.

In some cases, a constant diameter metallic knitted stent blank may be positioned over a mandrel having a tapered outer surface and one or more anti-migration feature forming elements, as generally indicated at block 102. The mandrel may be the mandrel 10, for example. In some cases, disposing a constant diameter metallic knitted stent blank in position over a mandrel includes stretching the constant diameter metallic knitted stent blank over the mandrel and allowing the constant diameter metallic knitted stent blank to conform to the varied diameter outer surface of the mandrel, such conforming to the various constant diameter regions and/or tapered diameter regions of the mandrel.

The one or more anti-migration feature forming elements (such as but not limited to the pins 18) may be engaged, as noted at block 104, in order to provide a desired shape prior to annealing, as indicated at block 106. In some cases, the one or more anti-migration feature forming elements are pins that are configured to be driven in a radially outward direction relative to the outer surface of the mandrel, and engaging the one or more anti-migration feature forming elements includes driving the pins in radially outward direction relative to the mandrel to urge the wire(s) or filament(s) engaged with the end of each of the pins in a radially outward direction relative to the knitted tubular structure of the stent. The mandrel and the stent thereon, with the anti-migration features formed, may then be subjected to an annealing or shape setting process. As seen at block 108, after the annealing or shape setting process, the one or more anti-migration feature forming elements may be disengaged in order to remove the shaped stent from the mandrel. In some cases, disengaging the one or more anti-migration feature forming elements comprises permitting the pins to move in an inward direction relative to the mandrel.

In some cases, once the shaped metallic stent has been removed from the mandrel, a constant diameter biodegradable knitted stent blank may be positioned over a mandrel having a tapered outer surface and one or more anti-migration feature forming elements, as generally indicated at block 110. In some cases, disposing a constant diameter biodegradable knitted stent blank in position over a mandrel includes stretching the constant diameter biodegradable knitted stent blank over the mandrel and allowing the constant diameter biodegradable knitted stent blank to conform to the varied diameter outer surface of the mandrel, such conforming to the various constant diameter regions and/or tapered diameter regions of the mandrel. The one or more anti-migration feature forming elements may be engaged, as noted at block 112, in order to provide a desired shape prior to annealing, as indicated at block 114.

In some cases, the annealing process for the biodegradable knitted stent blank may involve lower temperatures than that used for the metallic knitted stent blank. The mandrel and the stent thereon, with the anti-migration features formed, may then be subjected to an annealing or shape setting process. As seen at block 116, after the annealing or shape setting process, the one or more anti-migration feature forming elements may be disengaged in order to remove the shaped biodegradable stent from the mandrel. In some cases, disengaging the one or more anti-migration feature forming elements comprises permitting the pins to move in an inward direction relative to the mandrel. In some cases, while not illustrated, the shaped biodegradable stent may be disposed about or within the shaped metallic stent.

In some embodiments, the knitted stent 70 may be formed from any desired material, such as a biocompatible material including biostable, bioabsorbable, biodegradable or bioerodible materials. For instance, the knitted stent 70 may be formed of a metallic material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof. In some cases, the mandrel 10 may be formed of a material that is thermally stable and does not materially expand at the temperatures used in annealing the knitted stent 70. In some cases, for example, the mandrel 10 may be formed of a metallic material such as stainless steel, titanium or a nickel-titanium alloy. In some cases, the mandrel 10 may be formed of a ceramic material In some embodiments, the knitted stent 70 may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

Those skilled in the art will recognize that aspects of the present disclosure may be manifested in a variety of forms other than the specific embodiments described and contemplated herein. Accordingly, departure in form and detail may be made without departing from the scope of the present disclosure as described in the appended claims.

What is claimed is:

1. A mandrel comprising:
a mandrel body including:
a main bore extending within the mandrel body along a longitudinal axis of the mandrel body; and
a plurality of apertures formed in the mandrel body and radially disposed about the longitudinal axis of the mandrel body, the plurality of apertures extending directly into the main bore;
a plurality of movable pins radially disposed about the longitudinal axis of the mandrel body, each movable pin outwardly extendable from one of the plurality of apertures; and
an actuation element threadably engageable with the main bore extending within the mandrel body and including a tapered surface configured to engage the plurality of movable pins, the actuation element being actuatable along the longitudinal axis relative to the mandrel body such that the tapered surface supports the plurality of movable pins extended from the more plurality of apertures to form an anti-migratory stent, wherein each of the plurality of movable pins is configured to extend from one of the plurality of apertures at an acute angle relative to the longitudinal axis of the mandrel body.

2. The mandrel of claim 1, wherein the mandrel body comprises:
a first stent shaping segment having a first diameter;
a second stent shaping segment having a second diameter less than the first diameter; and
a tapered segment disposed between the first stent shaping segment and the second stent shaping segment, the tapered segment defining a tapered surface that angles from the first stent shaping segment to the second stent shaping segment.

3. The mandrel of claim 2, further comprising a third stent shaping segment releasably securable to the second stent shaping segment, the third stent shaping segment having a third diameter greater than the second diameter.

4. The mandrel of claim 2, wherein the plurality of apertures are equally spaced circumferentially about the tapered segment and extend through the tapered surface.

5. The mandrel of claim 2, wherein the corresponding apertures extend through the tapered segment and are configured to enable the pins to extend orthogonally to a tapered surface of the tapered segment.

6. The mandrel of claim 2, wherein the corresponding apertures extend through the tapered segment and are configured to enable the pins to extend at varying angles relative to a tapered surface of the tapered segment.

7. The mandrel of claim 1, wherein at least some of the plurality of pins have equal lengths.

8. The mandrel of claim 1, wherein an end of each of the plurality of movable pins includes a recessed slot configured to accommodate a wire of a stent being shaped on the mandrel.

9. A mandrel for forming a stent with a tapered outer profile and anti-migration features, the mandrel comprising:
   a mandrel body including:
      a first stent shaping segment having a first diameter and a first threaded aperture extending within the first stent shaping segment along a longitudinal axis of the mandrel body;
      a second stent shaping segment having a second diameter less than the first diameter and a second threaded aperture extending within the second stent shaping segment along the longitudinal axis of the mandrel body;
      a tapered segment disposed between the first stent shaping segment and the second stent shaping segment, the tapered segment including a tapered surface surrounding the longitudinal axis; and
      a plurality of apertures extending through only the tapered surface and radially disposed about the longitudinal axis of the mandrel body;
   a mandrel cap releasably securable to the second stent shaping segment, the mandrel cap including a third stent shaping segment having a third diameter greater than the second diameter;
   a plurality of movable pins, each of the plurality of movable pins configured to extend radially outwardly of the longitudinal axis from one of the plurality of apertures at an acute angle relative to the longitudinal axis of the mandrel body, the plurality of movable pins configured to form the anti-migration features in the stent; and
   an actuation element including:
      a tapered end configured to engage the plurality of movable pins; and
      a threaded body configured to threadingly engage the first threaded aperture;
   wherein rotating the actuation element causes the actuation element to advance along the longitudinal axis of the mandrel body into the first stent shaping segment such that the tapered end drives the plurality of movable pins in an outward direction.

10. The mandrel of claim 9, wherein the third diameter is equal to the first diameter.

11. The mandrel of claim 9, wherein at least some of the plurality of pins have equal lengths.

12. The mandrel of claim 9, wherein at least some of the plurality of pins have differing lengths.

13. The mandrel of claim 9, wherein an end of each of the plurality of movable pins includes a recessed slot configured to accommodate a wire of a stent being shaped on the mandrel.

14. The mandrel of claim 9, wherein the plurality of apertures extend through the tapered segment and are configured to enable the pins to extend orthogonally to a tapered surface of the tapered segment.

15. The mandrel of claim 9, wherein the plurality of apertures extend through the tapered segment and are configured to enable the pins to extend at varying angles relative to a tapered surface of the tapered segment.

16. A mandrel comprising:
   a mandrel body including:
      a first stent shaping segment having a first diameter, a second stent shaping segment having a second diameter different from the first diameter, and a tapered segment disposed between the first and second stent shaping segments, the tapered segment defining a tapered surface that angles from the first stent shaping segment to the second stent shaping segment;
      a main bore extending within the mandrel body along a longitudinal axis of the mandrel body; and
      a plurality of apertures extending through the tapered surface of the mandrel body and radially disposed about the longitudinal axis of the mandrel body, the plurality of apertures extending directly into the main bore;
   a plurality of movable pins radially disposed about the longitudinal axis and outwardly extendable from the plurality of apertures; and
   an actuation element engageable with the main bore extending within the mandrel body and including a tapered surface configured to engage the plurality of movable pins, the actuation element being actuatable relative to the mandrel body along the longitudinal axis of the mandrel body such that the tapered surface supports the plurality of movable pins extended from the plurality of apertures to form an anti-migratory stent, wherein each of the plurality of movable pins is configured to extend from one of the plurality of apertures at an acute angle relative to the longitudinal axis of the mandrel body.

17. The mandrel of claim 16, wherein the plurality of apertures are configured to enable the pins to extend orthogonally to a tapered surface of the tapered segment.

18. The mandrel of claim 16, wherein the plurality of apertures are configured to enable the pins to extend at varying angles relative to a tapered surface of the tapered segment.

19. The mandrel of claim 16, wherein an end of each of the plurality of movable pins includes a recessed slot configured to accommodate a wire of a stent being shaped on the mandrel.

* * * * *